US011007029B2

(12) United States Patent
Lutzow et al.

(10) Patent No.: US 11,007,029 B2
(45) Date of Patent: May 18, 2021

(54) METHOD AND APPARATUS FOR POSITIONING A WORKSTATION FOR CONTROLLING A ROBOTIC SYSTEM

(71) Applicant: Titan Medical Inc., Toronto (CA)

(72) Inventors: Thomas Andrew Lutzow, Providence, RI (US); Daniel Bacher, Boston, MA (US)

(73) Assignee: Titan Medical Inc., Toronto (CA)

( * ) Notice: Subject to any disclaimer, the term of this patent is extended or adjusted under 35 U.S.C. 154(b) by 169 days.

(21) Appl. No.: 15/780,207

(22) PCT Filed: Dec. 13, 2016

(86) PCT No.: PCT/CA2016/000316
§ 371 (c)(1),
(2) Date: May 30, 2018

(87) PCT Pub. No.: WO2017/124170
PCT Pub. Date: Jul. 27, 2017

(65) Prior Publication Data
US 2018/0353254 A1   Dec. 13, 2018

Related U.S. Application Data (60) Provisional application No. 62/280,230, filed on Jan. 19, 2016.

(51) Int. Cl.
*A61B 34/00*    (2016.01)
*G06F 3/01*     (2006.01)
*H03K 17/965*   (2006.01)

(52) U.S. Cl.
CPC .............. *A61B 34/74* (2016.02); *A61B 34/25* (2016.02); *G06F 3/011* (2013.01); *H03K 17/965* (2013.01); *A61B 2034/258* (2016.02)

(58) Field of Classification Search
CPC ... A61B 34/00; A61B 34/25; A61B 2034/258; A61B 34/35; A61B 34/37; A61B 34/70;
(Continued)

(56) References Cited

U.S. PATENT DOCUMENTS 5,174,223 A   12/1992   Nagy et al.
5,224,429 A    7/1993   Borgman et al.
(Continued)

OTHER PUBLICATIONS

International Search Report received in PCT Application No. PCT/CA2016/000316, dated Mar. 21, 2017.
(Continued)

*Primary Examiner* — Ahmed M Farah
(74) *Attorney, Agent, or Firm* — Knobbe Martens Olson & Bear, LLP (57) ABSTRACT

A method for positioning an input device of a workstation for use by a seated user in controlling a robotic surgery system is disclosed. The input device is operable to generate input signals representing a position of a hand controller moveable within an input device workspace. The method involves determining a vertical position of the hand controller within the input device workspace for an input signal received from the input device while a seated user's hand is grasping the hand controller in an initialization position defined with respect to the user's body. The method also involves determining a user ergonomic height of the input device based on the vertical position of the hand controller at the initialization position, and causing a platform of the workstation on which the input device is mounted to move vertically with respect to a base of the workstation to position the input device at the ergonomic height.

22 Claims, 6 Drawing Sheets

(58) Field of Classification Search
CPC .............. A61B 34/74; A61B 2034/472; A61B 2034/473; A61B 2034/474; A61B 34/77; A61B 2034/742; A61B 2034/743; A61B 2034/744; H03K 17/94; H03K 17/965; H03K 17/967; G06F 3/01; G06F 3/02; G06F 3/0216
USPC .......................................... 901/2, 6–8, 11–18
See application file for complete search history.

(56) References Cited

U.S. PATENT DOCUMENTS

| | | | |
|---|---|---|---|
| 5,605,311 A | 2/1997 | McGrath | |
| 8,120,301 B2* | 2/2012 | Goldberg | A61B 34/30 318/581 |
| 8,939,500 B2 | 1/2015 | Voight | |
| 9,587,878 B2* | 3/2017 | Paydar | G16H 20/13 |
| 10,092,092 B2 | 10/2018 | Koch | |
| 10,126,720 B2 | 11/2018 | Liu | |
| 10,219,871 B2 | 3/2019 | Mirbagheri et al. | |
| 10,398,521 B2* | 9/2019 | Itkowitz | A61B 1/00006 |
| 10,617,479 B2 | 4/2020 | Itkowitz et al. | |
| 10,717,194 B2* | 7/2020 | Griffiths | A61B 34/76 |
| 10,806,531 B2* | 10/2020 | Berry | A61B 34/37 |
| 2010/0185211 A1* | 7/2010 | Herman | A61B 90/50 606/130 |
| 2010/0225209 A1 | 9/2010 | Goldberg | |
| 2011/0120351 A1 | 5/2011 | Shoenfeld | |
| 2012/0085267 A1 | 4/2012 | Kenny | |
| 2014/0096706 A1* | 4/2014 | Labrosse | G05B 19/048 108/21 |
| 2014/0243849 A1 | 8/2014 | Saglam et al. | |
| 2017/0065477 A1 | 3/2017 | Jagger | |
| 2018/0147106 A1 | 5/2018 | Soundararajan | |
| 2018/0353245 A1 | 12/2018 | Mccloud | |
| 2019/0357990 A1 | 11/2019 | Lutzow et al. | |

OTHER PUBLICATIONS

Written Opinion received in PCT Application No. PCT/CA2016/000316, dated Mar. 21, 2017.

* cited by examiner

METHOD AND APPARATUS FOR POSITIONING A WORKSTATION FOR CONTROLLING A ROBOTIC SYSTEM

CROSS-REFERENCE TO RELATED APPLICATION

This application is a U.S. National Phase Application under 35 U.S.C. 371 of International Application No. PCT/CA2016/000316, filed on Dec. 13, 2016 and published as WO 2017/124170 A1 on Jul. 27, 2017, which claims priority to U.S. Provisional Application No. 62/280230, filed on Jan. 19, 2016. The entire disclosures of all of the above applications are incorporated herein by reference.

BACKGROUND

1. Field

This disclosure relates generally to a workstation for controlling a robotic system and more particularly to positioning an input device of the workstation with respect to a user.

2. Description of Related Art

In robotic systems, such as surgical robotic systems, a workstation may be provided to control a remotely located instrument through user input provided to an input device on the workstation. The user may be required to operate the workstation for an extended period of time, and the comfort of the user may thus be of concern since user fatigue may result.

SUMMARY

In accordance with one disclosed aspect there is provided a method for positioning an input device of a workstation for use by a seated user in controlling a robotic surgery system, the input device being operable to generate input signals representing a position of a hand controller moveable within an input device workspace. The method involves determining a vertical position of the hand controller within the input device workspace for an input signal received from the input device while a seated user's hand is grasping the hand controller in an initialization position defined with respect to the user's body. The method also involves determining a user ergonomic height of the input device based on the vertical position of the hand controller at the initialization position, and causing a platform of the workstation on which the input device is mounted to move vertically with respect to a base of the workstation to position the input device at the ergonomic height.

Determining the user ergonomic height may involve determining a vertical offset to the current height of the input device that will produce a pre-defined vertical position of the hand controller within the input device workspace when the input device is positioned at the ergonomic height.

Causing the platform to move vertically may involve causing the platform to move vertically over a vertical distance corresponding to the vertical offset.

Causing the platform to move vertically may involve causing the platform to move vertically in a direction associated with the vertical offset while successively receiving input signals from the input device representing the current position of the hand controller within the input device workspace, and causing the platform to discontinue vertical movement when the current position of the hand controller in the input device workspace may be proximate the pre-defined vertical position of hand controller.

The initialization position may involve the user's hand grasping the hand controller in one of a position with the user's wrist resting on the user's knee, a position with the user's wrist resting on a portion of the user's thigh proximate the knee, a position with the user's forearms held in a generally horizontal orientation, and a position with the user's arms held outstretched in a generally horizontal orientation.

The method may involve displaying a message on a display of the workstation, the message prompting the user to grasp and position the hand controller input device in the initialization position.

Determining the user ergonomic height may involve determining the user ergonomic height of the input device in response to actuation of a user actuable button by the user indicating that the hand controller is being held in the initialization position.

The method may involve receiving user input of a change to the user ergonomic height of the input device based on the user's preference and causing the platform to move vertically with respect to a base of the workstation to position the input device at the user directed ergonomic height.

The method may involve receiving a user identification identifying the user and saving information associated with the user directed ergonomic height in a user database for the identified user.

The platform of the workstation may be operably configured to move vertically within a vertical motion range and the method may further involve, when the workstation is initialized at startup, causing the platform to move to one of a vertical position such that the platform is positioned at a center position within the vertical motion range, a pre-defined ergonomic height determined to be suitable for an average user, and a user directed vertical position based on the user's preference of an identified user.

The input device may include a right input device operable to receive input from the user's right hand and may further include a left input device operable to receive input from the user's left hand, and determining the user ergonomic height may involve determining the user ergonomic height based on the vertical position of one of the left and right hand controllers at the initialization position.

The input device may include a right input device operable to receive input from the user's right hand and may further include a left input device operable to receive input from the user's left hand, and determining the user ergonomic height may involve determining the user ergonomic height based on a combination of the vertical positions of the left and right hand controllers when positioned at respective initialization positions.

In accordance with another disclosed aspect there is provided a workstation apparatus including an input device operable to generate input signals representing a position of a hand controller moveable within an input device workspace input device for controlling a robotic surgery system. The apparatus includes a base for supporting the workstation, and a platform mounted on the base for vertical movement with respect to the base, the input device being mounted on the platform. The apparatus also includes an actuator configured to cause vertical movement of the platform in response to receiving a control signal. The apparatus further includes a processor circuit operably configured to determine a vertical position of the hand controller within the input device workspace for an input signal received from the input device while a seated user's hand is grasping the hand controller in an initialization position defined with respect to the user's body, determine a user ergonomic height of the input device based on the vertical position of the hand controller at the initialization position, and produce the control signal for causing the actuator to move the platform to position the input device at the ergonomic height.

The processor circuit may be operably configured to determine the user ergonomic height by determining a vertical offset to the current height of the input device that will produce a pre-defined vertical position of the hand controller within the input device workspace when the input device is positioned at the ergonomic height.

The processor circuit may be operably configured to cause the actuator to move the platform over a vertical distance corresponding to the vertical offset.

The processor circuit may be operably configured to cause the actuator to move the platform in a direction associated with the vertical offset while successively receiving input signals from the input device representing the current position of the hand controller within the input device workspace, and cause the actuator to discontinue vertical movement of the platform when the current position of the hand controller in the input device workspace is proximate the pre-defined vertical position of hand controller.

The initialization position may include the user's hand grasping the hand controller in one of a position with the user's wrist resting on the user's knee, a position with the user's wrist resting on a portion of the user's thigh proximate the knee, a position with the user's forearms held in a generally horizontal orientation, and a position with the user's arms held outstretched in a generally horizontal orientation.

The workstation may include a display and the processor circuit may be operably configured to display a message on the display prompting the user to grasp and position the hand controller input device in the initialization position.

The processor circuit may be operably configured to determine the user ergonomic height in response to actuation of a user actuable button by the user indicating that the hand controller is being held in the initialization position.

The processor circuit may be operably configured to receive user input of a change to the user ergonomic height of the input device based on the user's preference and to causing the platform to move vertically with respect to a base of the workstation to position the input device at the user directed ergonomic height.

The apparatus may include a user database stored in a memory in communication with the processor circuit and the processor circuit may be operably configured to receive a user identification identifying the user and save information associated with the user directed ergonomic height in a user database for the identified user.

The platform of the workstation may be operably configured to move vertically within a vertical motion range and the processor circuit is operably configured to, when the workstation is initialized at startup, cause the platform to move to one of a vertical position such that the platform is positioned at a center position within the vertical motion range, a pre-defined ergonomic height determined to be suitable for an average user, and a user directed vertical position based on the user's preference of an identified user.

The input device may include a right input device operable to receive input from the user's right hand and may further include a left input device operable to receive input from the user's left hand, and the processor circuit may be operably configured to determine the user ergonomic height by determining the user ergonomic height based on the vertical position of one of the left and right hand controllers at the initialization position.

The input device may include a right input device operable to receive input from the user's right hand and may further include a left input device operable to receive input from the user's left hand, and the processor circuit may be operably configured to determine the user ergonomic height by determining the user ergonomic height based on a combination of the vertical positions of the left and right hand controllers when positioned at respective initialization positions.

The workstation may include at least one forearm support for receiving and supporting the user's forearm during operation of the input device and the forearm support may be coupled to the platform.

The workstation may include at least one display for providing visual feedback to the user and the display may be coupled to the platform.

Other aspects and features will become apparent to those ordinarily skilled in the art upon review of the following description of specific disclosed embodiments in conjunction with the accompanying figures.

BRIEF DESCRIPTION OF THE DRAWINGS

In drawings which illustrate disclosed embodiments.

DETAILED DESCRIPTION

Figure 1:
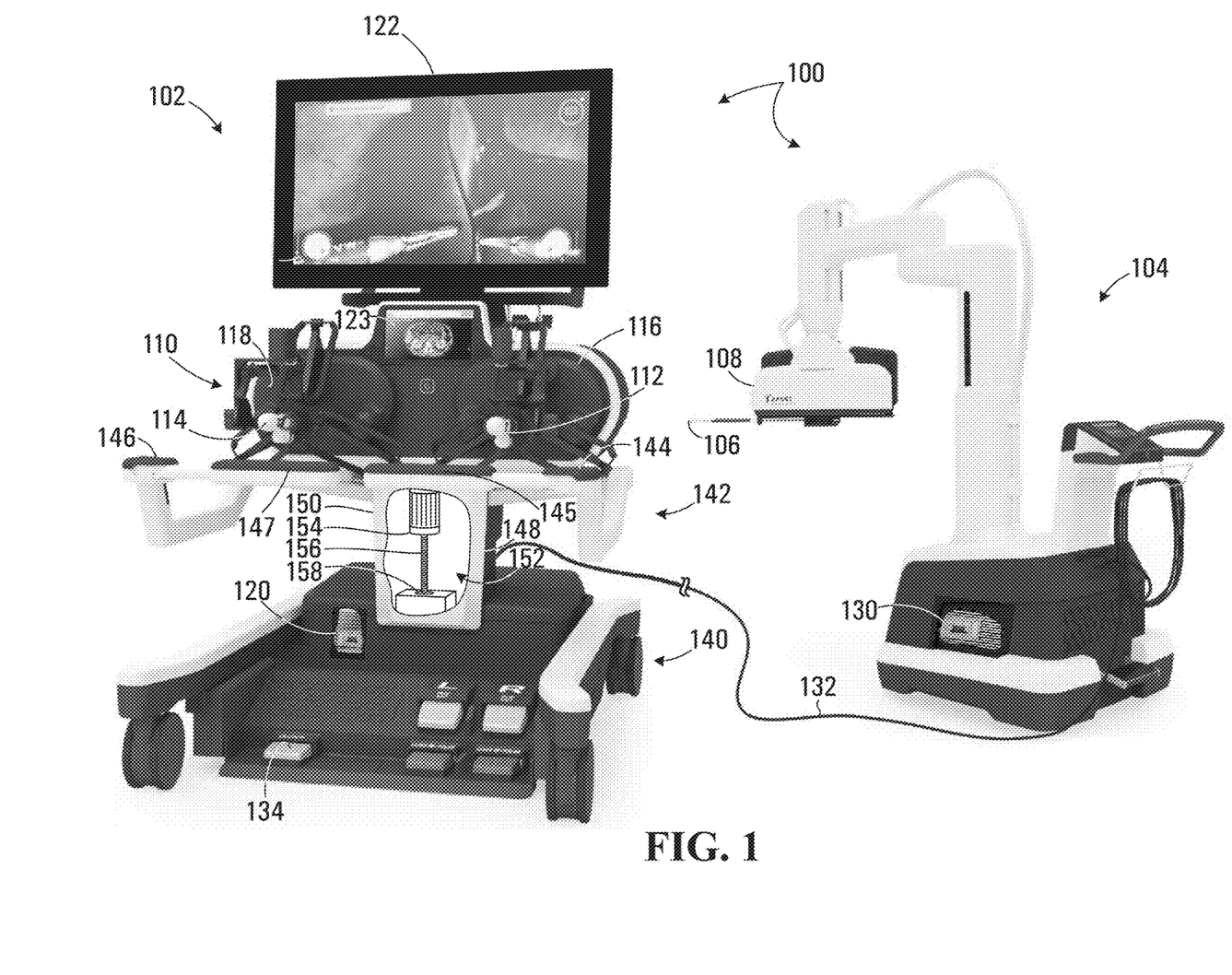
FIG. 1 is a perspective view of a workstation and instrument cart of a robotic surgery system in accordance with one disclosed embodiment.

Referring to FIG. 1, a robotic surgery system is shown generally at 100. The system 100 includes a workstation 102 and an instrument cart 104. The instrument cart 104 includes at least one instrument 106 mounted on a moveable instrument mount 108 that houses an instrument drive (not shown) for manipulating the instrument.

The workstation 102 includes an input device 110 for use by a user (generally a surgeon) for controlling the instrument 106 via the instrument drive to perform surgical operations on a patient. The input device 110 may be implemented using a haptic interface device available from Force Dimension, of Switzerland, for example. The input device 110 includes a right input device 116 and a left input device 118 for controlling respective right and left instruments 106 (not shown). The right input device 116 includes a hand controller 112 and the left input device 118 includes a hand controller 114, the hand controllers being mechanically coupled to the respective input devices. The input devices 116 and 118 thus generate input signals representing positions of the hand controllers 112 and 114 within the input device workspace. The workstation 102 also includes a workstation processor circuit 120, which is in communication with the input devices 116 and 118 for receiving the input signals.

The instrument cart 104 includes an instrument processor circuit 130 for controlling the instrument 106. In this embodiment the instrument processor circuit 130 is in communication with the workstation processor circuit 120 via an interface cable 132 for transmitting signals between the workstation processor circuit 120 and the instrument processor circuit 130. In other embodiments communication between the workstation processor circuit 120 and the processor circuit 130 may be wireless or via a computer network, and the workstation 102 and may even be located remotely from the instrument cart 104. Input signals are generated by the right and left input devices 116 and 118 in response to movement of the hand controllers 112 and 114 by the user within an input device workspace and the instrument 106 is spatially positioned in a surgical workspace in response to the input signals.

The workstation 102 also includes a display 122 in communication with the workstation processor circuit 120 for displaying real time images and/or other graphical depictions of the surgical workspace produced by a camera (not shown) associated with the instrument 106. The display 122 may further be operable to provide other visual feedback and/or instructions to the user. A second auxiliary display 123 may be utilized to display auxiliary surgical information to the user (surgeon), displaying, for example, patient medical charts and pre-operation images. The workstation 102 further includes a footswitch 134, which is actuable by the user to provide input signals to the workstation processor circuit 120. In one embodiment the signal provided to the workstation processor circuit 120 inhibits movement of the instrument 106 while the footswitch 134 is depressed.

In the embodiment shown, the workstation 102 includes a base 140 having a pedestal 148 extending upwardly from the base. The workstation 102 also includes a platform 142 having a column 150. The pedestal 148 supports the column 150 for vertical movement of the column and platform 142 with respect to the base 140. The input device 110 is mounted on the platform 142, and in this embodiment the display 122 and a pair of supports 144 and 146 for supporting the user's arms are also mounted on the platform. In this embodiment the supports 144 and 146 include respective elbow supports 145 and 147 that are operable to swivel in to support the user's elbows. The input device 110, display 122, auxiliary display 123, and supports 144 and 146 are thus all vertically moveable with respect to the base.

The column 150 houses an actuator 152 operably configured to cause vertical movement of the platform 142. In this embodiment, the actuator 152 includes a motor 154 coupled to a leadscrew 156. The leadscrew 156 is received within a leadscrew nut 158 and rotation of the leadscrew raises or lowers the platform 142 with respect to the base 140 when the motor 154 is actuated. The actuator 152 facilitates movement of the platform 142 over a vertical motion corresponding to a length of the leadscrew 156.

Figure 2:
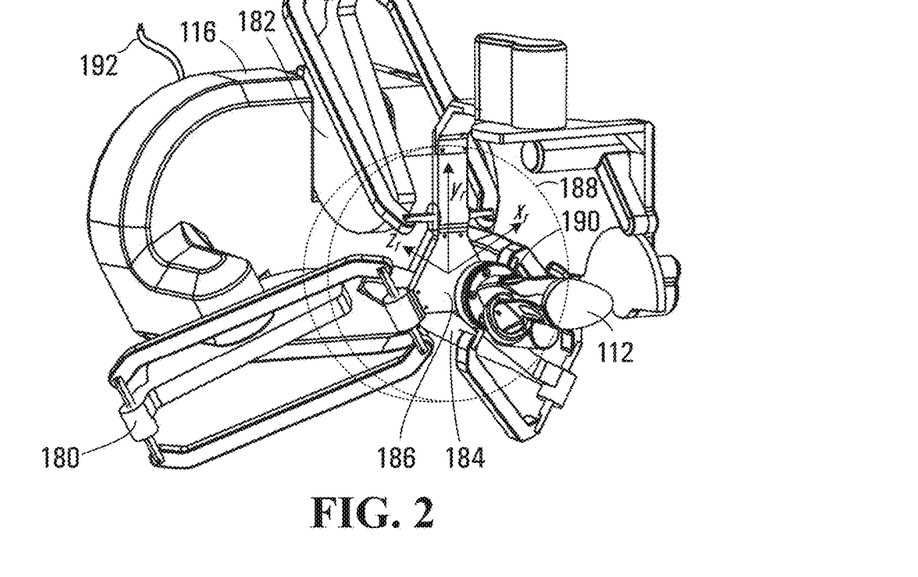
FIG. 2 is a perspective view of an input device of the workstation shown in FIG. 1.

The right input device 116 is shown in more detail in FIG. 2. Referring to FIG. 2, the input device 116 includes three moveable arms 180, 182, and 184. The hand controller 112 is coupled via a gimbal mount 186 to the moveable arms 180, 182, and 184, which confine movements of the hand controller to within a input device workspace 188. In this embodiment the input device workspace 188 is generally hemispherical. The input device 116 includes sensors (not shown) that sense the position of each of the arms 180, 182, and 184 and rotation of the hand controller 112 and produces signals representing a current position of the hand controller in the input device workspace 188 and a rotational orientation of the hand controller relative to an input device Cartesian reference frame $x_r$, $y_r$, $z_r$. In this embodiment, the position and orientation signals are transmitted as input signals via a USB connection 192 to the workstation processor circuit 120. In the embodiment shown the hand controller 112 includes a user actuable button 190, which produces additional input signals for transmission to the workstation processor circuit 120.

Figure 3:
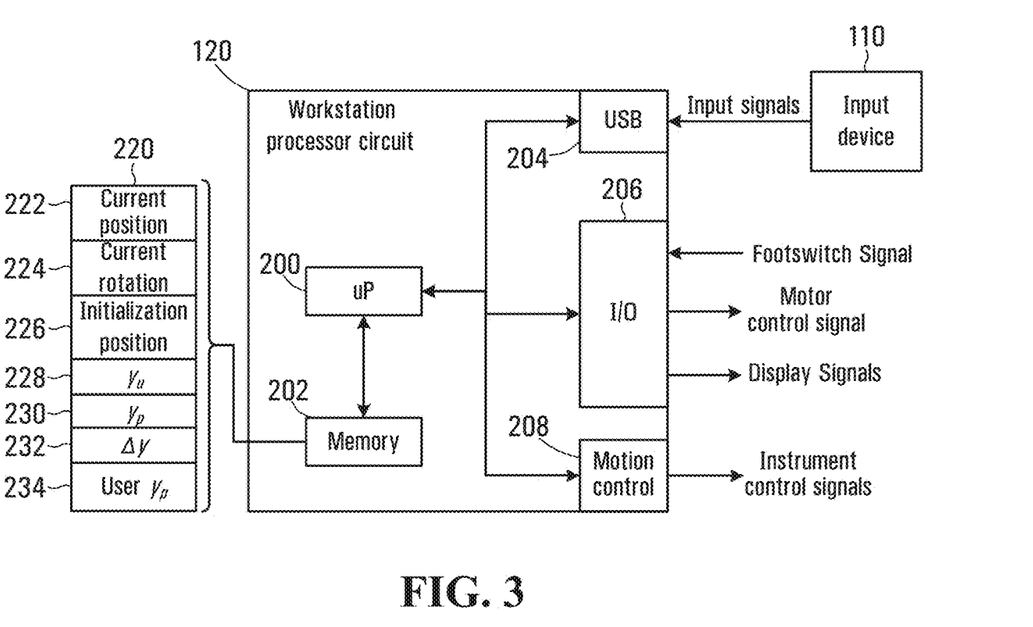
FIG. 3 is a block diagram of a processor circuit of the workstation shown in FIG. 1.

A block diagram of the processor circuit 120 of the system 100 is shown in FIG. 3. Referring to FIG. 3 the workstation processor circuit 120 includes a microprocessor 200. The workstation processor circuit 120 also includes a workstation memory 202, a USB interface 204, an input/output 206 and a motion control interface 208, all of which are in communication with the microprocessor 200. The workstation memory 202 includes a plurality of storage locations 220 for storing data values generated during operation of the system 100. The input/output 206 includes an input for receiving input signals from the footswitch 134 and also includes an output for producing an actuation signal for controlling the motor 154 to raise or lower the platform 142 and an output for producing display signals for driving the display 122 and auxiliary display 123.

In this embodiment the input device 110 communicates using a USB protocol and the USB interface 204 receives input signals produced by the input device in response to movements of the hand controllers 112 and 114. The microprocessor 200 processes the input signals and causes the motion control interface 208 to transmit control signals, which are conveyed to the instrument processor circuit 130 via the interface cable 132. The instrument processor circuit 130 processes the control signals and produces drive signals for moving the instrument 106. The workstation processor circuit 120 thus acts as a master subsystem for receiving user input, while the instrument processor circuit 130 and instrument 106 act as a slave subsystem in responding to the user input.

Figure 4:
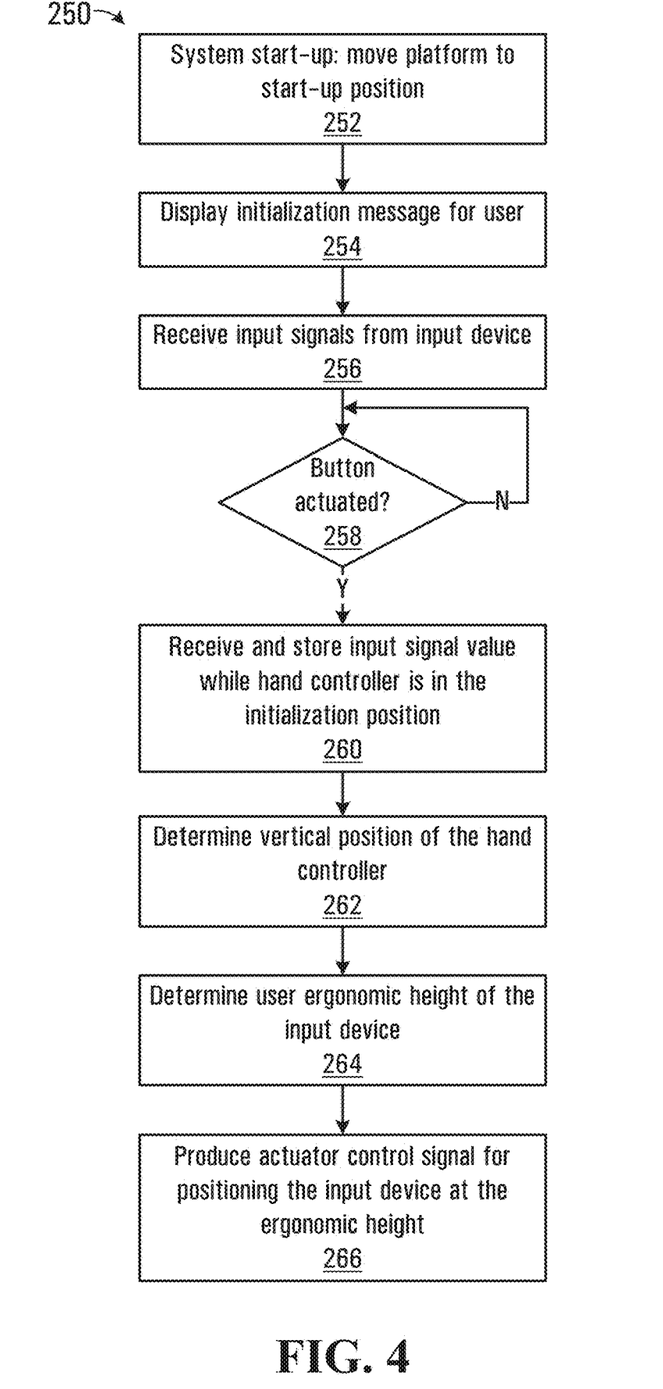
FIG. 4 is a flowchart depicting blocks of code for directing the processor circuit shown in FIG. 3 to perform functions related to positioning the input device shown in FIG. 2.

Referring to FIG. 4, a flowchart depicting blocks of code for directing the processor circuit 120 to perform functions related to positioning the input device 110 for use by a seated user is shown generally at 250. The actual code to implement each block may be written in any suitable program language, such as C, C++, C#, Java, and/or assembly code, for example.

The process 250 begins at block 252 when the system goes through a start-up procedure. In this embodiment, as part of the start-up procedure, the microprocessor 200 causes the platform 142 to move to a start-up position. As an example, the start-up position may be a vertical position that positions the platform at a center position within the vertical motion range provided by the leadscrew 156, a pre-defined ergonomic height determined to be suitable for an average user, or a user directed vertical position based on a last user's preference.

Figure 5:
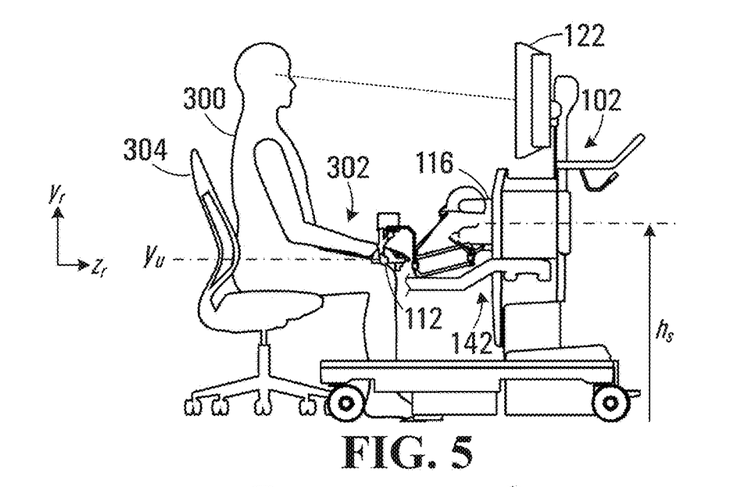
FIG. 5 is a side view of the workstation and a user seated in an initialization position.

Block 254 then directs the microprocessor 200 to cause an initialization message to be displayed on the display 122. The initialization message may include a direction to the user to assume an initialization position. Referring to FIG. 5, a user 300 is shown seated in an initialization position 302 in front of the workstation 102 with their feet placed on the ground. The user 300 is seated on a chair 304 and is holding the hand controller 112 with the wrist resting on a portion of the user's thigh proximate the knee, which provides a reasonably repeatable initialization position with respect to the user's body. In FIG. 5, the support 144 of the platform 142 is omitted for purposes of illustration. The user 300 will have already adjusted the height of the chair 304 prior to having moved up to the workstation 102. In other embodiments, the initialization position 302 may be otherwise defined, such as the user's wrist resting on the user's knee, the user's forearms being held in a generally horizontal orientation, or the user's arms being held outstretched in a generally horizontal orientation. The height of the chair 304 may thus be selected for the user's comfort rather than in accordance with the start-up height $h_s$ of the input device 116 of the workstation 102. In some embodiments, the initialization message displayed on the display 122 or auxiliary display 123 may include a graphic depicting the initialization position 302 shown in FIG. 5 to aid the user.

Block 256 then directs the microprocessor 200 to receive input signals from either or both of input devices 116 and 118. In the description following, it is assumed that the process is performed for the right hand controller 112, but in other embodiments the left hand controller 114 may be used or a combination of both left and right hand controllers may be used to define the initialization position. In general the input device 116 sequentially generates and transmits input signals representing the current position of the hand controller 112 within the input device workspace 188. The input signals may be in the form of a position vector and a rotation matrix representing the current position and rotation of the hand controller 112. The USB interface 204 of the workstation processor circuit 120 receives the input signals and the microprocessor 200 writes the values of the current position and rotation into storage locations 222 and 224 of the plurality of storage locations 220 shown in FIG. 3. The USB interface 204 of the workstation processor circuit 120 may also receive an input signal representing the state of the user actuable button 190.

The process 250 then continues at block 258, which directs the microprocessor 200 to determine whether the user actuable button 190 has been actuated by the user indicating the hand controller 112 is in the initialization position 302. If the user actuable button 190 has not been actuated, block 256 directs the microprocessor 200 back to the start of block 256, which is repeated while waiting for a change in state of the input signal produced by the user actuable button 190 being actuated by the user, indicating that the user is in the initialization position 302. If at block 258, the user actuable button 190 has been actuated, the microprocessor 200 is directed to block 260. In other embodiments, block 258 may cause the microprocessor 200 to respond to a state of the input signal received at the input/output 206 from the footswitch 134 when determining whether the hand controller is in the initialization position 302.

Block 260 then directs the microprocessor 200 to receive the input signal values as described above in connection with block 256 and to copy the value of the received current position in the storage location 222 to an initialization position storage location 226 (shown in FIG. 3). Block 262 then directs the microprocessor 200 to determine the vertical position of the hand controller 112 within the input device workspace 188 corresponding to the initialization position 302. Referring back to FIG. 2, the vertical position of the hand controller $y_u$, which is specific to the user 300, is simply the y-coordinate of the current hand controller position within the input device workspace 188 (i.e. $x_r$, $y_r$, $z_r$ coordinate space).

The process 250 then continues at block 264, which directs the microprocessor 200 to determine a user ergonomic height of the input device 116 based on the vertical position $y_u$ of the hand controller 112 at the initialization position 302. In one embodiment the user ergonomic height is defined in terms of a vertical offset to the current height of the input device 112 that will produce a pre-defined vertical position $y_p$ of hand controller within the input device workspace 188 when the input device is positioned at the ergonomic height. As an example, for the situation shown in FIG. 5, if the vertical position of the hand controller $y_u$ is higher than the pre-defined vertical position $y_p$, then the input device 116 is too low and should be moved upwards by a vertical distance $\Delta y$. If the vertical position of the hand controller $y_u$ is higher than the pre-defined vertical position $y_p$, then the input device 116 is too high and should be moved downwardly by a vertical offset $\Delta y$.

Figure 6:
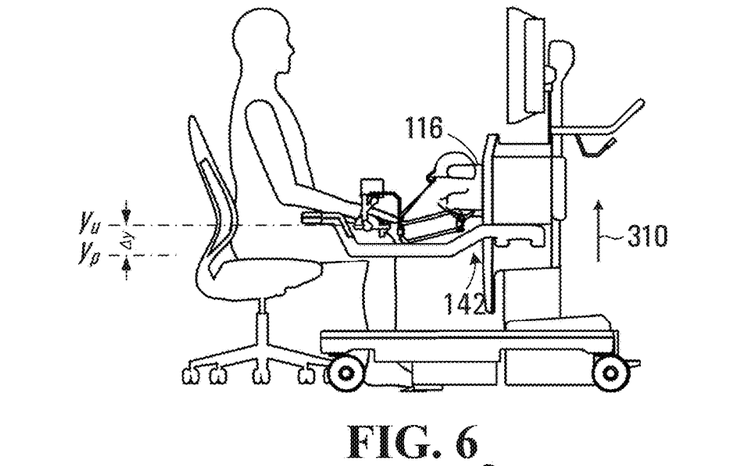
FIG. 6 is a further side view of the workstation console and a user seated in an initialization position with a platform moving toward an ergonomic height.

The process 250 then continues at block 266, which directs the microprocessor 200 to produce an actuator control signal for causing the actuator 152 to move the platform 142 by the vertical offset $\Delta y$ to position the input device at the determined ergonomic height. Referring to FIG. 6, the platform 142 is shown moving upwardly in the direction of the arrow 310 to position the input device 116 at the ergonomic height $h_e$, where $h_e$ is given by:

$$h_e = h_s + \Delta y.$$

Figure 7:
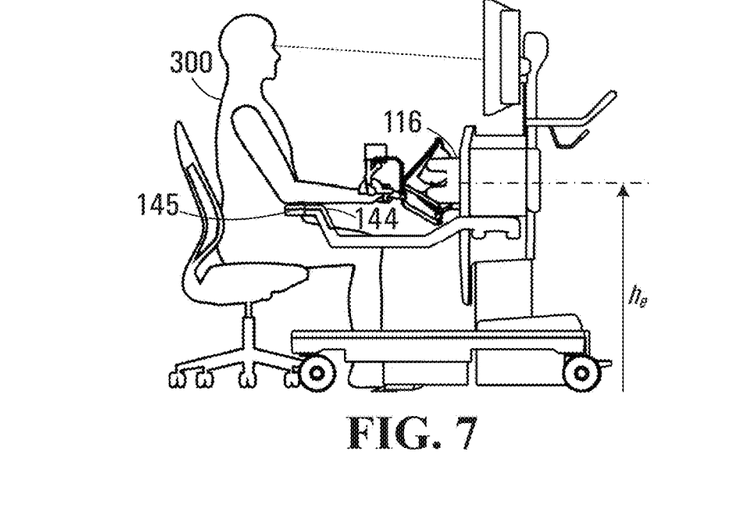
FIG. 7 is a side view of the workstation console and a user seated in an operating position with the platform and input device positioned at the ergonomic height.

In one embodiment, the motor 154 of the actuator 152 may be implemented using a stepper motor that in combination with the leadscrew 156 is operable to provide a relatively precise vertical movement of the platform 142 corresponding to the vertical offset $\Delta y$ to place the right input device 116 at the ergonomic height $h_e$. Referring to FIG. 7, the platform 142 is shown with the input device 116 located at the ergonomic height $h_e$. The user 300 then places their elbow on the elbow support 145 and should find that the right input device 116 is positioned at a comfortable height for further operation.

Figure 8:
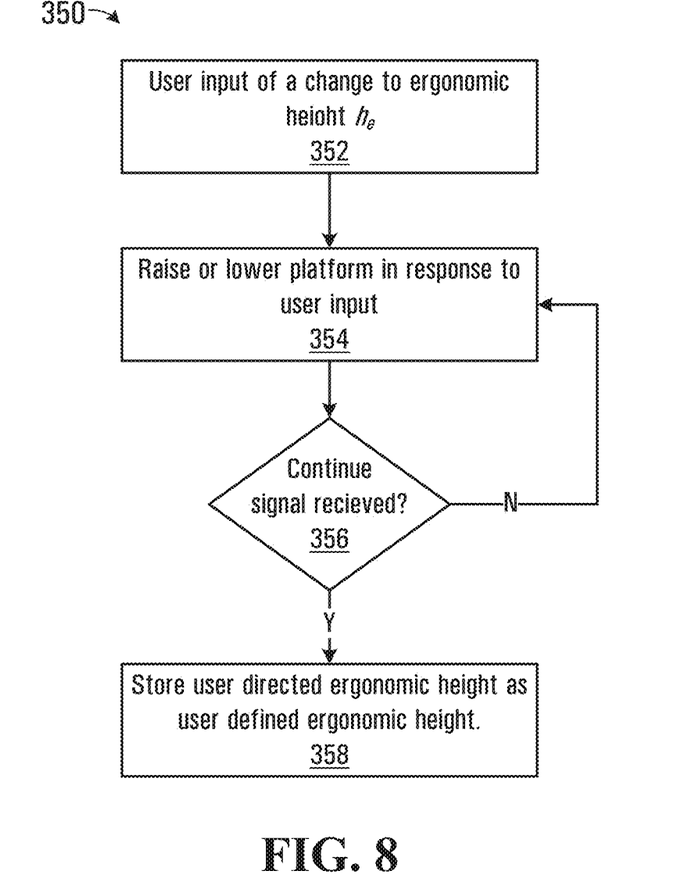
FIG. 8 is a flowchart depicting blocks of code for directing the processor circuit shown in FIG. 3 to perform functions related to receiving a change to the ergonomic height.

In some cases the user 300 may find that the ergonomic height $h_e$ set by the workstation processor circuit 120 is not to their personal preference. Referring to FIG. 8, a process for receiving user input of a change to the user ergonomic height of the input device 112 based on the user's preference is shown at 350. The process follows block 266 of the process 250 and begins at block 352, by causing the microprocessor 200 to receive input from the user 300 requesting a change to the ergonomic height. For example, the user actuable button 190 may be implemented as an up/down toggle button and the user 300 may actuate the button to move the platform 142 upwardly or downwardly from the ergonomic position. Block 354 then directs the microprocessor 200 to cause the motor 154 of the actuator 152 to be actuated at a slow speed to raise or lower the platform 142 while the user actuates the user actuable button 190. Block 356 then directs the microprocessor 200 to determine whether a "continue" signal has been received indicating that the user is satisfied with the change to the ergonomic position $h_e$. The continue signal may be received from another button (not shown) provided on the hand controller 112 or from another input means, such as the footswitch 134. If at block 356 the "continue" signal has not been received, the microprocessor 200 is directed back to block 354 and the block is repeated while the user makes further changes to the ergonomic position.

If at block 356 the "continue" signal has been received, the microprocessor 200 is directed to block 358, which directs the microprocessor to copy the current hand controller position in the storage location 222 to a user database store 236 as a user directed $y_p$. In one embodiment, the start-up procedure implemented at block 252 of the process 250 may involve a user identification process that identifies the user 300 operating the workstation 102 and the user directed ergonomic position may be stored along with the user identification as a user $y_p$. When the same user 300 subsequently uses the system, the platform 142 may then be automatically positioned to the user's preference at block 252 of the process 250, and the remaining blocks 254-266 may be omitted.

Figure 9:
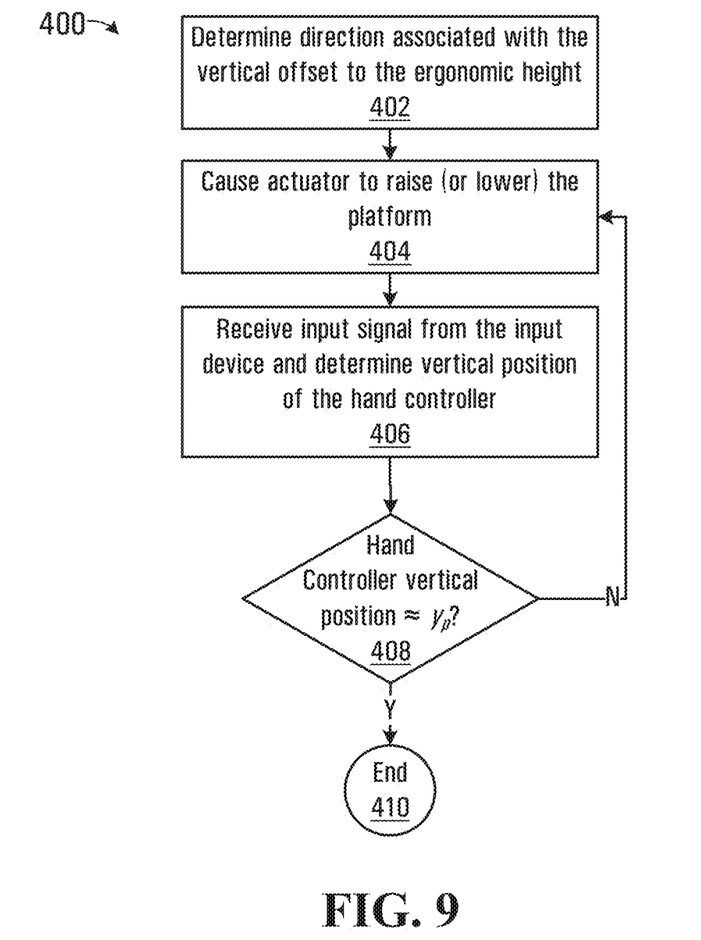
FIG. 9 is a is a flowchart depicting blocks of code for directing the processor circuit shown in FIG. 3 to perform functions related to raising or lowering the platform to position the platform at the ergonomic height.

In an alternative embodiment, block 266 of the process 250 may be implemented to position the input device 116 at the ergonomic height using a process shown at 400 in FIG. 9. The process 400 begins at block 402, which directs the microprocessor 200 to determine a direction in which the platform 142 must move to reduce the vertical offset Δy between the current position of the hand controller $y_u$ and the pre-defined position of the hand controller $y_p$ at the desired ergonomic height $h_e$. Block 404 then directs the microprocessor 200 to cause the actuator 152 to raise or lower the platform 142 accordingly. Block 406 then directs the microprocessor 200 to receive the input signal from the hand controller 112 and to determine a current vertical position of the hand controller. The process then continues at block 408, which directs the microprocessor 200 to determine whether the hand controller vertical position is approximately equal to the pre-defined vertical position $y_p$. If the current vertical position of the hand controller is not yet at the pre-defined vertical position $y_p$, then block 408 directs the microprocessor 200 back to block 404 and blocks 404 to 408 are repeated. If at block 408, the hand controller vertical position is approximately equal to the pre-defined vertical position $y_p$, block 458 directs the microprocessor to 410 and the process 400 ends. The process 400 may be suitable for embodiments where the actuator 152 does not provide for precise vertical movement of the platform 142. For example, the motor 154 may be implemented using a simple direct current or other motor that has limited ability to control rotational movements of the leadscrew 156. Alternatively, the process 400 may be employed where an alternative actuator such as a hydraulic cylinder, which uses fluid pressure to raise or lower the platform 142.

By mounting the display 122 on the platform 142, the display is also placed at an ergonomic height. For example, in FIG. 5, the user 300 must look downwardly to view the center of the display, while in FIG. 7 the angle is substantially reduced. In some embodiments, the display 122 may be mounted on the platform 142 so as to permit an initial vertical adjustment of the display to accommodate a range of user preferences.

The above embodiments have been described with reference to receiving input from the right input device 116. In other embodiments, the processes 250, 350, and 400 may equally well be implemented using inputs from the left input device 118, or a combination of inputs from the left and right input devices. For example, the user 300 may be instructed to place both hands in the respective initialization positions while grasping the respective hand controllers 112 and 114, and the input signals from both the right input device 116 and left input device 118 may be received and combined by averaging, for example.

The disclosed embodiments have the advantage of positioning the input device 110, display 122, and pair of supports 144 and 146 at an ergonomic height that is determined with respect to the particular user. Users that are taller than average or shorter than average will thus first find a comfortable seated position, whereafter the workstation 102 will adjust the height of the 142 to suit the user.

While specific embodiments have been described and illustrated, such embodiments should be considered illustrative of the invention only and not as limiting the invention as construed in accordance with the accompanying claims.

What is claimed is:

1. A method for positioning an input device of a workstation for use by a user in controlling a robotic surgery system, the input device being operable to generate input signals representing a position of a hand controller moveable within an input device workspace, the method comprising:
   determining a vertical position of the hand controller within the input device workspace for an input signal received from the input device while a user's hand is grasping the hand controller in an initialization position defined with respect to user's body;
   determining a user ergonomic height of the input device based on the vertical position of the hand controller at the initialization position;
   causing a platform of the workstation on which the input device is mounted to move vertically with respect to a base of the workstation to position the input device at the user ergonomic height, wherein the platform of the workstation is operably configured to move vertically within a vertical motion range, and
   when the workstation is initialized at startup, causing the platform to move to at least one of:
      a vertical position such that the platform is positioned at a center position within the vertical motion range;
      a pre-defined ergonomic height determined to be suitable for an average user; or
      a user directed vertical position based on user's preference of an identified user.

2. The method of claim 1 wherein determining the user ergonomic height comprises determining a vertical offset to a current height of the input device that will produce a pre-defined vertical position of the hand controller within the input device workspace when the input device is positioned at the user ergonomic height.

3. The method of claim 2 wherein causing the platform to move vertically comprises causing the platform to move vertically over a vertical distance corresponding to the vertical offset.

4. The method of claim 2 wherein causing the platform to move vertically comprises:
   causing the platform to move vertically in a direction associated with the vertical offset while successively receiving input signals from the input device representing a current position of the hand controller within the input device workspace; and
   causing the platform to discontinue vertical movement when the current position of the hand controller in the input device workspace is proximate the pre-defined vertical position of hand controller.

5. The method of claim 1 wherein the initialization position comprises the user's hand grasping the hand controller in one of:
a position with a user's wrist resting on a user's knee;
a position with the user's wrist resting on a portion of a user's thigh proximate the user's knee;
a position with a user's forearms held in a generally horizontal orientation; or
a position with a user's arms held outstretched in a generally horizontal orientation.

6. The method of claim 1 further comprising displaying a message on a display of the workstation, the message prompting the user to grasp and position the hand controller in the initialization position.

7. The method of claim 1 wherein determining the user ergonomic height comprises determining the user ergonomic height of the input device in response to actuation of a user actuable button by the user indicating that the hand controller is being held in the initialization position.

8. The method of claim 1 further comprising receiving user input of a change to the user ergonomic height of the input device based on user's preference and causing the platform to move vertically with respect to a base of the workstation to position the input device at the user directed ergonomic height.

9. The method of claim 8 further comprising receiving a user identification identifying the user and saving information associated with the user directed ergonomic height in a user database for the identified user.

10. The method of claim 1 wherein the input device comprises a right hand controller operable to receive input from a user's right hand and further comprising a left hand controller operable to receive input from a user's left hand, and wherein determining the user ergonomic height comprises determining the user ergonomic height based on the vertical position of at least one of the left or right hand controllers being positioned at the initialization position.

11. The method of claim 1 wherein the input device comprises a right hand controller operable to receive input from a user's right hand and further comprising a left hand controller operable to receive input from a user's left hand, and wherein determining the user ergonomic height comprises determining the user ergonomic height based on a combination of the vertical positions of the left and right hand controllers when positioned at respective initialization positions.

12. A method for positioning an input device of a workstation for use by a user in controlling a robotic surgery system, the input device being operable to generate input signals representing a position of a hand controller moveable within an input device workspace, the method comprising:
determining a vertical position of the hand controller within the input device workspace for an input signal received from the input device while a user's hand is grasping the hand controller in an initialization position defined with respect to user's body;
determining a user ergonomic height of the input device based on the vertical position of the hand controller at the initialization position, determining the user ergonomic height comprising determining the user ergonomic height of the input device in response to actuation of a user actuable button by the user indicating that the hand controller is being held in the initialization position; and
causing a platform of the workstation on which the input device is mounted to move vertically with respect to a base of the workstation to position the input device at the user ergonomic height.

13. The method of claim 12 wherein determining the user ergonomic height comprises determining a vertical offset to a current height of the input device that will produce a pre-defined vertical position of the hand controller within the input device workspace when the input device is positioned at the user ergonomic height.

14. The method of claim 13 wherein causing the platform to move vertically comprises causing the platform to move vertically over a vertical distance corresponding to the vertical offset.

15. The method of claim 13 wherein causing the platform to move vertically comprises:
causing the platform to move vertically in a direction associated with the vertical offset while successively receiving input signals from the input device representing a current position of the hand controller within the input device workspace; and
causing the platform to discontinue vertical movement when the current position of the hand controller in the input device workspace is proximate the pre-defined vertical position of hand controller.

16. The method of claim 12 wherein the initialization position comprises the user's hand grasping the hand controller in one of:
a position with a user's wrist resting on a user's knee;
a position with the user's wrist resting on a portion of a user's thigh proximate the user's knee;
a position with a user's forearms held in a generally horizontal orientation; or
a position with a user's arms held outstretched in a generally horizontal orientation.

17. The method of claim 12 further comprising displaying a message on a display of the workstation, the message prompting the user to grasp and position the hand controller in the initialization position.

18. The method of claim 12 further comprising receiving user input of a change to the user ergonomic height of the input device based on user's preference and causing the platform to move vertically with respect to a base of the workstation to position the input device at the user directed ergonomic height.

19. The method of claim 18 further comprising receiving a user identification identifying the user and saving information associated with the user directed ergonomic height in a user database for the identified user.

20. The method of claim 12 wherein the input device comprises a right hand controller operable to receive input from a user's right hand and further comprising a left hand controller operable to receive input from a user's left hand, and wherein determining the user ergonomic height comprises determining the user ergonomic height based on the vertical position of at least one of the left or right hand controllers being positioned at the initialization position.

21. The method of claim 12 wherein the input device comprises a right hand controller operable to receive input from a user's right hand and further comprising a left hand controller operable to receive input from a user's left hand, and wherein determining the user ergonomic height comprises determining the user ergonomic height based on a combination of the vertical positions of the left and right hand controllers when positioned at respective initialization positions.

22. A method for positioning an input device of a workstation for use by a user in controlling a robotic surgery system, the input device being operable to generate input signals representing a position of a hand controller moveable within an input device workspace, the method comprising:
- determining a vertical position of the hand controller within the input device workspace for an input signal received from the input device while a user's hand is grasping the hand controller in an initialization position defined with respect to user's body;
- determining a user ergonomic height of the input device based on the vertical position of the hand controller at the initialization position; and
- causing a platform of the workstation on which the input device is mounted to move vertically with respect to a base of the workstation to position the input device at the user ergonomic height,
- wherein the input device comprises a right hand controller operable to receive input from a user's right hand and further comprising a left hand controller operable to receive input from a user's left hand, and
- wherein determining the user ergonomic height comprises determining the user ergonomic height based on the vertical position of at least one of the left or right hand controllers being positioned at the initialization position.

* * * * *